US010258680B2

(12) United States Patent
Szymanski et al.

(10) Patent No.: US 10,258,680 B2
(45) Date of Patent: Apr. 16, 2019

(54) CAMPYLOBACTER VACCINE

(71) Applicant: THE GOVERNORS OF THE UNIVERSITY OF ALBERTA, Edmonton (CA)

(72) Inventors: Christine Szymanski, Edmonton (CA); Harald Nothaft, Edmonton (CA)

(73) Assignee: The Governors of the University of Alberta, Edmonton, AB (CA)

(*) Notice: Subject to any disclaimer, the term of this patent is extended or adjusted under 35 U.S.C. 154(b) by 0 days.

(21) Appl. No.: 14/782,558

(22) PCT Filed: Apr. 4, 2014

(86) PCT No.: PCT/CA2014/050341
§ 371 (c)(1),
(2) Date: Oct. 5, 2015

(87) PCT Pub. No.: WO2014/161090
PCT Pub. Date: Oct. 9, 2014

(65) Prior Publication Data
US 2016/0045584 A1 Feb. 18, 2016

Related U.S. Application Data
(60) Provisional application No. 61/808,875, filed on Apr. 5, 2013.

(51) Int. Cl.
A61K 39/02 (2006.01)
C12P 19/26 (2006.01)
A23K 10/18 (2016.01)
A23L 33/135 (2016.01)
A61K 39/00 (2006.01)
A61K 39/106 (2006.01)

(52) U.S. Cl.
CPC .......... A61K 39/0208 (2013.01); A23K 10/18 (2016.05); A23L 33/135 (2016.08); C12P 19/26 (2013.01); A23V 2002/00 (2013.01); A61K 2039/106 (2013.01); A61K 2039/52 (2013.01); A61K 2039/521 (2013.01); A61K 2039/522 (2013.01); A61K 2039/523 (2013.01); A61K 2039/552 (2013.01); A61K 2039/55566 (2013.01); A61K 2039/58 (2013.01)

(58) Field of Classification Search
None
See application file for complete search history.

(56) References Cited

U.S. PATENT DOCUMENTS

| 6,866,847 B1 * | 3/2005 | Kelly-Aehle | A61K 9/0017 424/184.1 |
| 7,598,354 B2 | 10/2009 | Young et al. | |
| 2010/0062484 A1 * | 3/2010 | Aebi | C07K 14/205 435/69.1 |
| 2012/0100177 A1 | 4/2012 | Ilg et al. | |

FOREIGN PATENT DOCUMENTS

| WO | 2006119987 A2 | 11/2006 |
| WO | 2009089154 A2 | 7/2009 |
| WO | 2010/108682 A1 | 9/2010 |
| WO | 2011/097733 A1 | 8/2011 |
| WO | 2012/027850 A1 | 3/2012 |

OTHER PUBLICATIONS

Fisher et al. Applied and Environmental Microbiology vol. 77, No. 3, Feb. 2011, p. 871-p. 881.*
Feldman et al. The Journal of Biological Chemistry vol. 274, pp. 35129-35138, 1999.*
Whitfield et al. Molecular Microbiology (1997) (23 (4), 629-638.*
Dumont et al. Angew. Chem. Int. Ed. 2012, 51, 3143-3146.*
Franco et al. Journal of Bacteriology, May 1998, p. 2670-2675, vol. 180, No. 10.*
International Preliminary Report on Patentability issued in corresponding International Application No. PCT/CA2014/050341 dated Oct. 15, 2015 (2 pages).
International Search Report issued in corresponding application No. PCT/CA2014/050341 dated Jul. 4, 2014 (4 pages).
Written Opinion issued in corresponding application No. PCT/CA2014/050341 dated Jul. 4, 2014 (7 pages), Nov. 1, 2016.
Wacker et al.; N-linked glycosylation in Campylobacter jejuni and its functional transfer into E. coli, Science, Nov. 29, 2002, vol. 298, pp. 1790-1793 (5 pages).
Thommen, I. N., "Campylobacter N-glycan presenting Salmonella typhimurium: a new vaccine for broiler chickens?", Zurich Open Repository and Archive, University of Zurich, Dissertation, Vetsuisse Faculty, Jan. 1, 2011, 55 pages.
Buckles, E. L, et al., "PhoU enhances the ability of Extraintestinal Pathogenic Escherichia coli Strain CFT073 to Colonize the Murine Urinary Tract", Division of Infectious Diseases, Department of Medicine, Univeristy of Maryland School of Medicine, Jun. 20, 2005, 8 pages.
Daigle, F., "Identification of a Mutation in the pst-phoU Operon That Reduces Pathogenicity of an Escherichia coli Strain Causing Septicemia in Pigs", Universite de Monreal, Quebec, Canada, Dec. 1, 1995, 4 pages.
de Zoete, M. R., "Vaccination of Chickens against Campylobacter", ScienceDirect, Sep. 13, 2006, 10 pages.

(Continued)

Primary Examiner — Oluwatosin A Ogunbiyi
(74) Attorney, Agent, or Firm — Bennett Jones LLP

(57) ABSTRACT

The present application provides a vaccine composition comprising: bacteria engineered to express at least one N-glycan of Campylobacter, such as C. jejuni for example, or an N-glycan derivative thereof on its cell surface; and one or more of a physiologically acceptable diluent, excipient, adjuvant or carrier. The bacteria is Escherichia coli, Salmonella or any suitable bacteria that offers sufficient expression and improved immunogenic response. The vaccine composition can be formulated for administration to animals, such as poultry, including chickens.

12 Claims, 9 Drawing Sheets

(56) References Cited

OTHER PUBLICATIONS

Dwivedi, R., et al., "Generation of Free Oligosaccharides from Bacterial Protein N-Linked Glycosylation Systems", Biopolymers vol. 99, No. 10, May 7, 2013, 12 pages.
Hendrixson, D. R., et al., "Identification of Campylobacter jejuni genes Involved in Commensal Colonization of the Chick Gastrointestinal Tract", Molecular Microbiology, Dec. 22, 2003, 14 pages.
Lin, J., "Novel Approaches for Campylobacter Control in Poultry", Foodborne Pathogens and Disease, vol. 6, No. 7, Jan. 1, 2009, 12 pages.
Karlyshev, A. V., "The Campylobacter jejuni General Glycosylation System is Important for Attachment to Human Epithelial Cells and in the Colonization of Chicks", London School of Hygiene and Tropical Medicine, Univeristy of London, Aug. 19, 2003, 8 pages.
Katarzyna, E., et al., "Update on Campylobacter jejuni Vaccine Development for Preventing Human Campylobacteriosis", Expert Reviews, Jan. 1, 2009, 21 pages.
Kelly, J., et al, "Biosynthesis of the N-Linked Glycan in Campylobacter jejuni and Addition onto Protein through Block Transfer", institute for Biological Sciences, National Research Counsel of Canada, vol. 188, No. 7, Nov. 15, 2005, 8 pages.
Kwaga, J. K. P., et al, "A carAB Mutant of Avian Pathogenic *Escherichia coli* Serogroup O2 is Attenuated and Effective as a Live Oral Vaccine against Colibacillosis in Turkeys", American Society for Microbiology, vol. 62, No. 9, Sep. 1, 1994, 7 pages.
Larsen, J. C., et al., "N-Linked Protein Glycosylation is Required for Full Competence in Campylobacter jejuni 81-176", Department of Microbiology and Immunology, F. Edward Herbert School of Medicine, vol. 186, No. 19, Jan. 1, 2004, 7 pages.
Muller-Loennies, S., et al., "Idenitification of a Cross-reactive Epitope Widely Present in Lipopolysaccharide from Enterobacteria and Recognized by the Cross-Protective Monoclonal Antibody WN1 222-5", The Journal of Biological Chemistry, vol. 278, No. 28, Mar. 21, 2003, 11 pages.
Nothaft, H., et al., "Diversity in the Protein N- Glycosylation Pathways within the Campylobacter Genus", The American Society for Biochemistry and Molecular Biology, Inc., Jun. 18, 2012, 17 pages.
Szymanski, C. M., et al., "Campylobacter Protein Glycosylation Affects Host Cell Interactions", Enteric Diseases Program, Naval Medical Research Center, vol. 70, No. 4, Oct. 15, 2001, 3 pages.
Szymanski, C. M., et al., "Evidence for a System of General Protein Glycosylation in Campylobacter jejuni", Department of Biochemistry and Microbiology, University of Victoria, Dec. 28, 1998, 9 pages.
van Sorge, N. M., et al., "N-glycosylated Proteins and Distine Lipooligosaccharide Glycoforms of Campylobacter jejuni Target the Human C-Type Lectin Receptor MGL", Department of Infectious Diseases and Immunology, Utracht University, May 4, 2009, 14 pages.
Wyszynska, A., "Oral Immunization of Chickens with Avirulent *Salmonella* Vaccine Strain carrying C. jejuni 72Dz/92 cjaA gene Elicits Specific Humoral Immune Response Associated with Protection against Challenge with Wild-Type Campylobacter", www.sciencedirect.com, Apr. 1, 2003, 11 pages.
Young, N. M., et al., "Structure of the N-Linked Glycan Present on Multiple Glycoproteins in the Gram-Negative Bacterium, Campylobacter jejuni", The Journal of Biological Chemistry, Nov. 8, 2002, 11 pages.
Alemka, A., et al., "N-Glycosylation of Campylobacter jejuni Surface Proteins Promotes Bacterial Fitness", Infection and Immunity, vol. 81, No. 5, May 1, 2013, 9 pages.
Bada, t., et al., Construction of *Escherichia coli* K-12 in-Frame, Single-Gene Knockout Mutants: the Keio Collection, Molecular Systems and Biology, Sep. 28, 2005, 11 pages.
Bojer, M. S., et al., "Lack of the RNA Chaperone Hfg Attenuates Pathogenicity of Several *Escherichia coli* Pathotypes towards Caenorhabditis elegans", Department of Science, Systems and Models, Roskilde University, Mar. 12, 2012, 3 pages.
Bovarnick, M. A., et al., "The Influence of Certain Salts, Amino Acids, Sugars, and Proteins on the Stability of Rickettsiae", Department of Public Health Bacteriology, Harvard University School of Public Health, Jan. 13, 1950, 14 pages.
Wacker, M., et al, "N-Linked Glycosylation in Campylobacter jejuni and Its Functional Transfer into *E Coli*", Institute of Microbiology, Department of Biology, Swiss Federal Institute of Technology, Aug. 8, 2002, 5 pages.
Ilg, K. C., "Glysoenginerring and Glycosmimicry: Campylobacter jejuni Carbohydrate Structures on *Salmonella enterica* Serovar Typhimurium", A dissertation submitted to ETH Zurich, Jan. 1, 2009, 5 pages.
Communication Pursuant to Rule 114(2) EPC dated Jun. 14, 2016, in related European Application No. 14778134.8 (11 pages).
Extended European Search Report dated Sep. 29, 2016, in related European Application No. 14778134.8 (8 pages).
Feldman, M. F. et al., "Engineering N-linked Protein Glycosylation with Diverse O Antigen Lipopolysaccharide Structures in *Escherichia Coli*", The National Academy of Sciences of the USA, Feb. 22, 2005, Bol 102, No. 8; pp. 3016-3021 (6 pages).
Thommen, I. N., Campylobacter N-glycan presenting *Salmonella typhimurium*: a new vaccine for broiler chickens? Zurich Open Repository and Archive, University of Zurich, 2011, http://doi.org/10.5167/uzh-60771 (56 pages).
Office Action in related Chinese Patent Application No. 201480020298.0 dated Nov. 30, 2016 (19 pages).

* cited by examiner

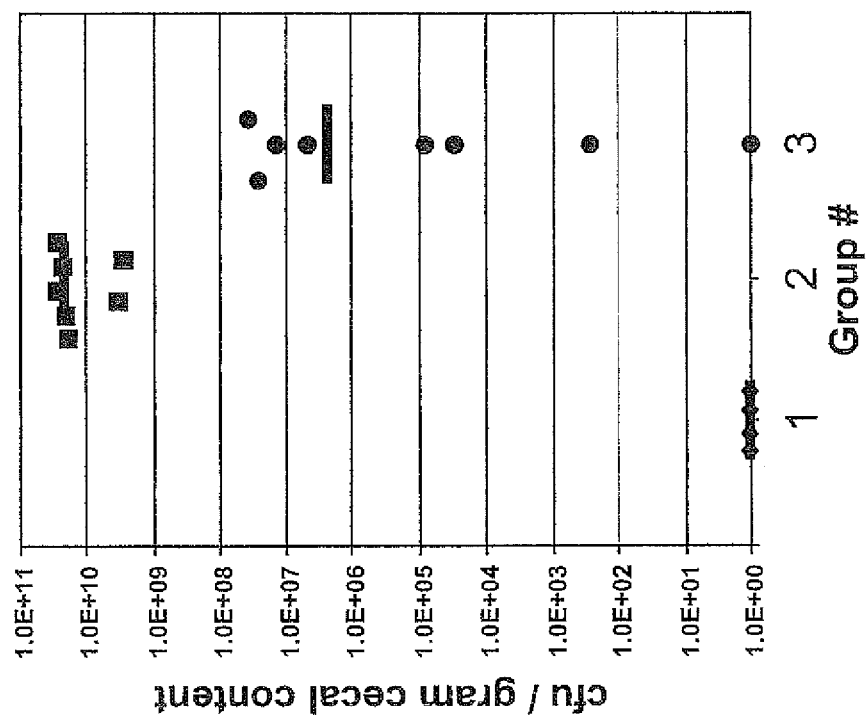

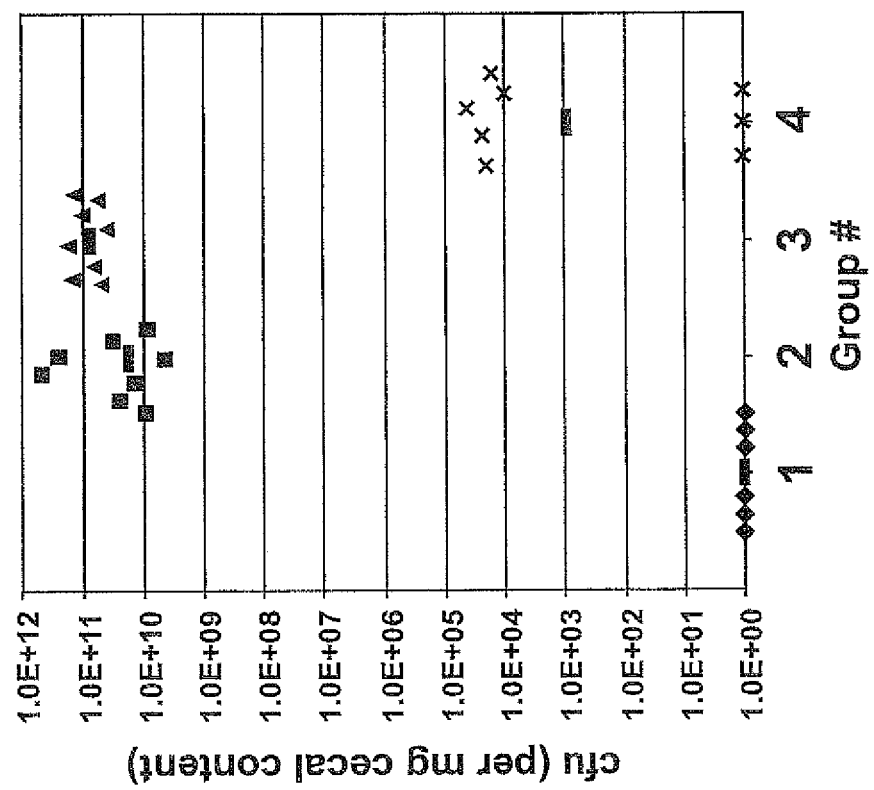

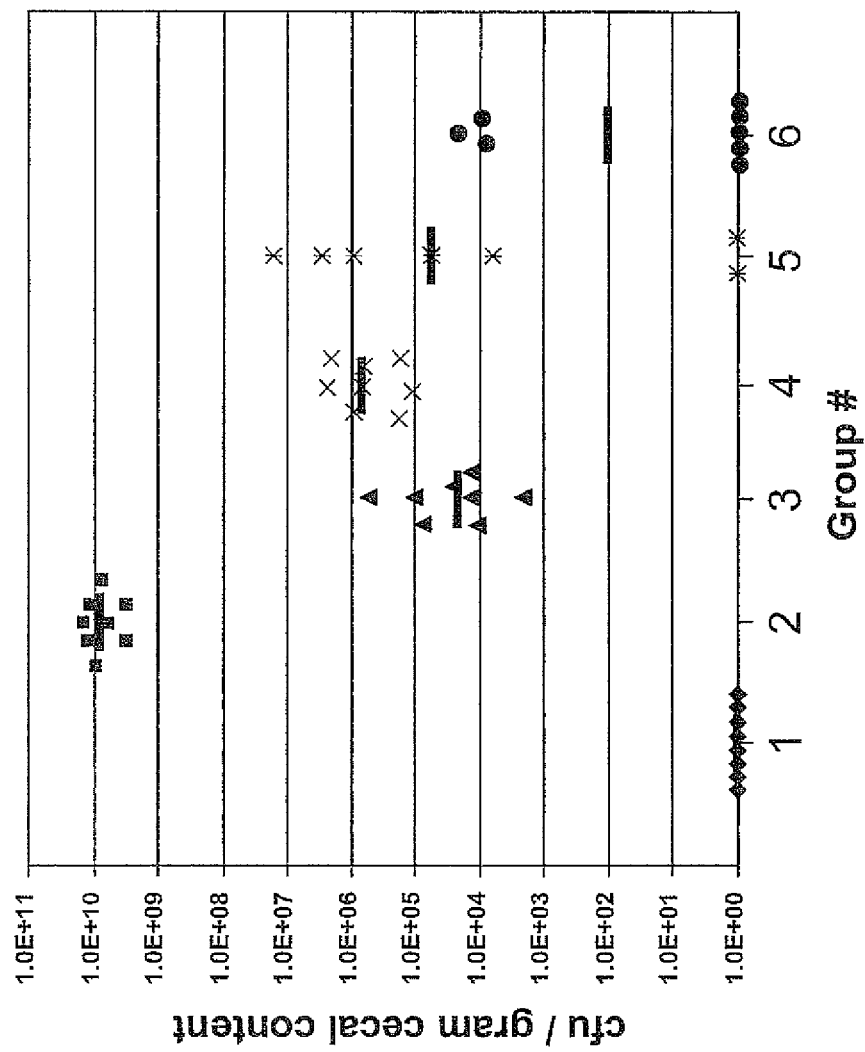

CAMPYLOBACTER VACCINE

FIELD OF THE INVENTION

The present invention pertains to campylobacter vaccines. More particularly, the present invention pertains to campylobacter vaccines comprising *Escherichia coli* cells expressing the *Campylobacter jejuni* heptasaccharide glycan derived from the N-glycosylation pathway.

BACKGROUND

The Gram-negative bacterium *Campylobacter* is the most common bacterial cause of human gastroenteritis in North America and many industrialized countries. *Campylobacter* is also a significant foodborne pathogen in livestock, including poultry, which are considered to be a major source of human campylobacteriosis. Thus, on-farm control of *Campylobacter* in poultry would reduce the risk of human exposure to this pathogen and have a significant impact on food safety and public health.

*Campylobacter* is endemic to many developing countries, mainly owing to poor sanitary conditions and close human contact with animals that are the reservoirs of the pathogen. A report by Katarzyna et al. Expert Rev. Vaccines 8: 625-645, 2009), suggests that in the United States, *Campylobacter* infections are the cause of 1.5 million (World Health Organization data) to 2.4 million (U.S. Centers for Disease Control data) disease cases each year. In addition, according to the World Health Organization, approximately 1% of the Western European population is annually infected by *Campylobacter* spp. Human infections are caused mainly by two species: *C. coli* and *C. jejuni*, which are responsible for over 95% of campylobacteriosis cases. Clinical manifestations of *Campylobacter* infections can range from asymptomatic cases to severe gastroenteritis, accompanied by sometimes long-lasting mucous, bloody, or watery diarrhea.

The publication of Jun Lin "Novel Approaches for *Campylobacter* Control in Poultry" (FOODBORNE PATHOGENS AND DISEASE, Volume 6, Number 7, pp. 755-765, 2009), incorporated herein by reference, discusses various strategies for reducing *Campylobacter* infection in poultry. Lin suggests three general strategies to control *Campylobacter* in poultry at the farm level: (1) reduction of environmental exposure (biosecurity measures), (2) an increase in poultry's host resistance to reduce *Campylobacter* carriage in the gut (e.g., competitive exclusion, vaccination, and host genetics selection), and (3) the use of antimicrobial alternatives to reduce and even eliminate *Campylobacter* from colonized chickens (e.g., bacteriophage therapy and bacteriocin treatment). Lin further states that except for biosecurity measures, the other intervention approaches are not commercially available and are still under development.

Elimination of these pathogens from livestock can serve as a means to reduce the incidence of infection in humans and prevent spread in farms animals. Vaccination on farms can also reduce the risk of human contamination from eating or handling animal products as well as contamination by fecal shedding of bacteria from livestock manure. Treatment of campylobacteriosis with antibiotics is also becoming increasingly challenging as antibiotic resistance of *Campylobacter* to previously effective antibiotics is becoming more common.

Glycosylation had once been considered to be specifically a eukaryotic phenomenon but was later shown to be widespread in both the Archaeal and Bacterial domains. Bacterial O- and N-linkages are formed with a wider range of sugars than those observed in eukaryotic glycoproteins. A general glycosylation pathway for proteins in Bacteria was first demonstrated in *C. jejuni*. (Szymanski et al. *Molecular Microbiology* 32: 1022-1030, 1999). The glycosylation machinery of *C. jejuni* has been characterized and has even been successfully transferred to E. coli (Wacker et al. Science, 298: 1790-1793, 2002) and active N-glycosylation of proteins was demonstrated (Young et al. *J Biol Chem*, 277: 42530-42539, 2002; Wacker et al. *Science*, 298: 1790-1793, 2002). The gene locus of *C. jejuni*, termed pgl (for protein glycosylation), is involved in the glycosylation of multiple proteins. Its mutational silencing results in loss of immunogenicity in multiple proteins, among many biological phenotypes.

U.S. Patent Application Publication 2006/0165728 A1, now U.S. Pat. No. 7,598,354, incorporated herein by reference, identifies a specific and highly immunogenic heptasaccharide that is present in a plurality of periplasmic and surface-exposed glycoproteins of *C. jejuni*. This heptasaccharide is common to at least several *Campylobacter* species and numerous strains that are important as human and veterinary pathogens (Nothaft et al. *Mol. Cell. Proteomics* 11: 1203-1219, 2012). The heptasaccharide has the following formula (I): GalNAc-α1,4-GalNAc-α1,4-[Glc-β-1,3] GalNAc-α1,4-GalNAc-α1,4-GalNAc-α1,3-diNAcBac, wherein diNAcBac (also termed di-N-acetylbacillosamine) is 2,4-diacetamido-2,4,6-trideoxy-D-glucopyranose, GalNAc is N-acetyl-galactosamine and Glc is glucose. This glycan moiety is a component of multiple glycoproteins. In *C. jejuni* the N-glycan is important for the interaction of *C. jejuni* with host cells. Mutations in the glycosylation machinery lead to decreased colonisation of intestinal tracts in mice and chickens. In *C. jejuni* the N-glycan is important for attachment and invasion of human epithelial cells (Szymanski et al. *Infect Immun* 70: 2242-2244, 2002), colonization of the intestinal tracts of mice and chickens (Kelly et al. *J Bacteriol* 188: 2427-2434, 2006; Szymanski et al. *Infect Immun* 70: 2242-2244, 2002; Hendrixson & DiRita, *Mol Microbiol* 52: 471-484, 2004; Karlyshev et al. *Microbiology* 150: 1957-1964, 2004), natural competence in strains with Type IV secretion systems (Larsen et al. *J Bacteriol* 186: 6508-6514, 2004) and for binding to the human macrophage C-type lectin, MGL (van Sorge et al, *Cell Microbiol* 11: 1768-1781, 2009). Moreover, *Campylobacter* surface N-glycans were shown to play protective roles against chicken gut proteases resulting in increased bacterial fitness (Alemka et al. *Infect Immun* 81: 1674-82, 2013).

U.S. Pat. No. 9,309,493 describes a *Salmonella enterica* strain comprising at least one pgl operon of *C. jejuni* or a functional derivative thereof and presenting at least one N-glycan of *C. jejuni*, or glycan derivative thereof, on its cell surface. This recombinant *S. enterica* is hypothesized to be useful in a vaccine against *Campylobacter* infections, particularly in livestock, such as poultry. However, unfortunately, subsequent publications have shown that while the recombinant *S. enterica* expressing the N-glycan from *Campylobacter* on its surface was able to colonize chickens without causing disease, there was no detectable humoral immune response in the vaccinated chickens against the *Campylobacter* N-glycan (Thommen "*Campylobacter* N-glycan presenting *Salmonella Typhimurium*: a new vaccine for broiler chickens?" Zurich Open Repository and Archive, University of Zurich, Dissertation, Vetsuisse Faculty, 2011). Furthermore, there was no reduction in colonization of *C. jejuni* in the vaccinated chickens upon infection with a *C. jejuni* challenge.

There remains a need for an effective vaccine for preventing and/or treating *Campylobacter* infections in humans and animals, in particular livestock, more particularly poultry.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide a vaccine against Campylobacter. In accordance with one aspect, there is provided a vaccine composition comprising bacteria engineered to express at least one N-glycan of *Campylobacter* or a glycan derivative thereof on its cell surface; and one or more of a physiologically acceptable diluent, excipient, adjuvant or carrier. In certain embodiments, the *Campylobacter* species is *C. jejuni*. The bacteria can be *Escherichia coli* or *Salmonella* and the engineered bacteria express the *C. jejuni* heptasaccharide on its surface.

In certain embodiments, the vaccine composition comprises live, engineered *E. coli*, or live, attenuated, inactivated or killed engineered *E. coli* cells. The composition can comprise a suspension of engineered bacteria in a suitable buffered diluent, such as phosphate buffered saline, and can be formulated for oral administration, in ovo administration, parenteral administration (e.g., by injection or infusion), or spraying, for example. The vaccine composition can also be formulated for addition to livestock feed, feed additives or water, and for administration to poultry, such as chickens.

In accordance with another aspect, there is provided a method of vaccinating an animal against *Campylobacter*, the method comprising administering to an animal a vaccine composition as described herein comprising bacteria engineered to express at least one N-glycan of *Campylobacter*, such as *C. jejuni*, or a glycan derivative thereof on its cell surface; and one or more of a physiologically acceptable diluent, excipient, adjuvant or carrier.

It is known that expression of the N-glycan on Salmonella does not induce a protective immune response. Surprisingly, the inventors found that *E. coli*—which is a very similar bacteria to *Salmonella*, and would have expected to obtain similar results—does indeed induce a protective immune response in chicken when expressing the N-glycan.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Definitions

Figure 1:
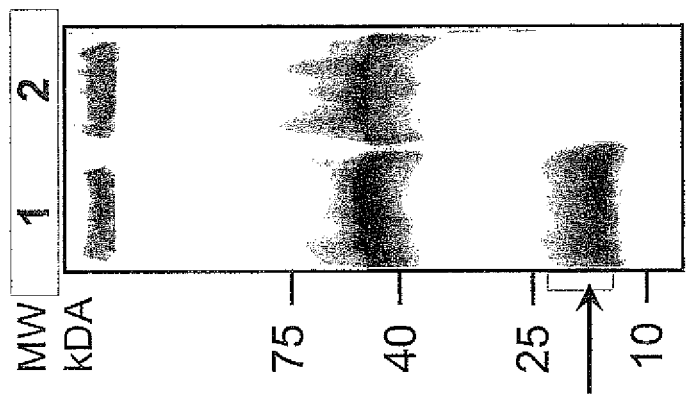
FIG. 1 shows *E. coli* proteinase K treated cell lysates from the *E. coli* polymerase mutant.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The terms "*C. jejuni* glycan", "*C. jejuni* heptasaccharide", "N-glycan heptasaccharide", "*Campylobacter* N-glycan", and "heptasaccharide," are used interchangeably herein to refer to a glycan moiety that is present in a plurality of surface-exposed glycoproteins and free oligosaccharides in multiple strains and species of *Campylobacter*. This glycan, in the case of *C. jejuni* and as exemplified herein, has the formula: GalNAc-α1,4-GalNAc-α1,4-[Glc-β-1,3]GalNAc-α1,4-GalNAc-α1,4-GalNAc-α1,3-diNAcBac, wherein diNAcBac is 2,4-diacetamido-2,4,6-trideoxy-D-glucopyranose. These terms can refer to glycosylation either by N-glycosylation or using sugars derived from N-glycosylation or other pathways. Recent work by the inventors has demonstrated that the *C. jejuni* N-glycan and free oligosaccharides are reasonably conserved across the thermophilic species of *Campylobacter* (Nothaft et al. *Mol. Cell. Proteomics* 11: 1203-1219, 2012), with some species producing a hexasaccharide derivative of the heptasaccharide, lacking the glucose branch. The use of alternate N-glycan structures and free oligosaccharides described by (Nothaft et al. *Mol. Cell. Proteomics* 11: 1203-1219, 2012) that are present in the non-thermophilic *Campylobacter* species, such as those described in PCT Publication WO/2011/097733, is also contemplated, and incorporated herein by reference.

The term "antigen" as used herein refers to a chemical or biological species that induces an immune response in an animal or human. In the presently described system, the antigen comprises the heptasaccharide of *Campylobacter jejuni* or an N-glycan derivative thereof. The term "N-glycan derivative" as used herein refers to derivatives of the heptasaccharide that induce an immune response in an animal similar to or better than that induced by the heptasaccharide itself. The N-glycan can be conjugated to carriers such as proteins (as described in PCT Application No WO 2012/027850) and lipids (Nothaft et al. *Mol. Cell. Proteomics* 11: 1203-1219, 2012, van Sorge et al. *Cell Microbiol* 11: 1768-1781, 2009), for example, or shorter or longer saccharide repeats of the heptasaccharide into a polysaccharide.

The term "vaccine" as used herein refers to a composition for improving immunity in animals or humans to certain microorganisms. The presently described vaccines can be used in a wide variety of animals, such as, for examples, ayes, such as poultry, as well as mammals. The microorganisms targeted by the presently described vaccine are of the genus *Campylobacter*.

The term "*Campylobacter*" as used herein refers to a genus of bacterium comprising any and all species of the genus *Campylobacter*. The various species of *Campylobacter* of this genus include, but are not limited to, *C.*

*jejuni, C. hominis, C. rectus, C. lari, C. fetus, C. coli, C. upsaliensis, C. fetus* subsp. *venerealis, C. fetus* subsp. *fetus, C. peloridis, C. lari* subsp. *concheus, C. sputorum, C. gracilis, C. showae, C. lanienae, C. curvus, C. helveticus, C. hyointestinalis* subsp. *hyointestinalis, C. hyointestinalis* subsp. *lawsonii, C. mucosalis, C. sputorum* bv. *paraureolyticus, C. sputorum* bv. *fecalis, C. ureolyticus, C. insulaenigrae, C. concisus, C. subantarcticus, C. avium, C. cuniculorum,* and *C. volucris.*

The present application provides a glycan, and immunologically active fragments thereof, that can be used as vaccines against *Campylobacter* infection in humans and animals. Such vaccines can be useful to prevent or neutralize *Campylobacter* infections in livestock thereby preventing this pathogen from entering the human food chain. In certain embodiments, the *C. jejuni* heptasaccharide and fragments thereof, optionally linked to an amino acid, oligopeptide, lipid or other suitable conjugate, can be used as a vaccine. For example, this vaccine can be used in any animal that is infected with *Campylobacters* for which the N-glycan can be expressed on the surface of *E. coli* as a Lipid A core fusion.

Vaccine Composition

The present application provides a vaccine composition comprising recombinant *E. coli* that has been engineered to express at least one *Campylobacter* N-glycan, or a heptasaccharide derivative thereof, on its surface. The recombinant *E. coli* is live, dead and/or attenuated.

As described above, the *Campylobacter* heptasaccharide is common to at least several *Campylobacter* species and numerous strains including species that are important as human and veterinary pathogens. It is a component of multiple glycoproteins, including, for example, *C. jejuni* Nos. Cj0114, Cj0200c, Cj0289c, Cj0367c, and others. This glycan moiety is also strongly immunogenic and as such this glycan (and related derivatives thereof and glycopeptides comprising the N-glycan or derivatives thereof) was identified as a good candidate for use as an antigen in a vaccine for immunization against multiple strains and species of *Campylobacter* in mammals, including humans and livestock, including chicken (U.S. Pat. No. 7,598,354).

*E. coli* is a Gram-negative bacterium that has an outer membrane covered in lipopolysaccharide (LPS), which contributes to the structural integrity of the bacteria and provides a physical barrier to protect the membranes. LPS is made up of three main components: Lipid A, the core and the o-antigen. Lipid A anchors the LPS to the outer membrane and the O-antigen is the outermost part of the LPS. The core is a branched oligosaccharide that bridges the Lipid A and O-antigen components of the LPS.

The *E. coli* strain useful in the preparation of the present vaccine composition is any strain that is or can be sufficiently attenuated to allow for its non-pathological administration to humans and/or animals in live or dead form. Other bacteria can be used such as *Salmonella* or other strains of *E. coli* that can offer sufficient expression and improved immunogenic response.

The term "pgl operon" as used herein refers to any physiologically active glycosylation cluster of *Campylobacter* genes capable of glycosylating homologous or heterologous structures produced by the *E. coli* strain employed in the vaccine composition. The pgl operon in *C. jejuni* encodes all enzymes necessary for the synthesis of the *C. jejuni* N-glycan heptasaccharide, its transport through the inner membrane and the transfer to proteins. PglD, E, F code for the enzymes involved in di-N-acetylbacillosamine biosynthesis, PglC transfers UDP-diN-acetylbacillosamine to undecaprenylphosphate and PglA, H and J add the GalNAc residues. The Glc branch is attached by PglI. The transfer across the inner membrane of the completed heptasaccharide occurs through action of PglK and the oligosaccharyltransferase PglB transfers the N-glycan to protein and also releases the heptasaccharide into the periplasm in its free form.

A functional derivative of a pgl operon is a cluster of genes derived from any *Campylobacter* pgl operon having deletions, mutations and/or substitutions of nucleotide(s) or whole genes but still capable of producing an oligo- or polysaccharide that can be linked to homologous or heterologous structures produced by the *E. coli* strain used in the vaccine composition. One or more pgl operons or derivatives thereof can be integrated into the chromosome of the *E. coli* strain or it/they can be introduced as part of at least one plasmid. Typically chromosomal integration is preferred because it is more stable compared to plasmid vectors, the loss of which could occur during propagation. It is noted that the *E. coli* strain can comprise more than one pgl operon or derivative thereof producing one or more N-glycans or derivative(s) thereof. In certain embodiments, the vaccine composition comprises an *E. coli* strain having more than one type of pgl operon resulting in more than one glycan structure being expressed on the surface of the recombinant *E. coli.* This can be advantageous for eliciting a more diverse immune response in a human or animal against different *Campylobacter* species. In an alternative embodiment, the vaccine composition comprises an *E. coli* strain having a single type of pgl operon resulting in one glycan structure being expressed on the surface of the recombinant *E. coli.* This can be advantageous for eliciting a specific immune response in a human or animal against a single *Campylobacter* species.

Optionally, the expression level of the *C. jejuni* glycan can be regulated by the use of different promoters or other regulatory elements upstream of the pgl operon, including, but not limited to, promoters of ribosomal protein genes, as well as promoters from antibiotic-resistance encoding genes like bla or similar and preferably strong promoters. This type of regulation is available for plasmid-encoded or chromosomally integrated pgl operons. Furthermore, plasmid stability can optionally be enhanced by including essential genes on the plasmid while deleting these genes in the genome of the *E. coli* strain employed in the vaccine composition.

In an alternative embodiment the pglB gene of the pgl operon is inactivated, meaning that the corresponding oligosaccharyltransferase B is either not expressed or at least enzymatically inactivated. The pglB gene product transfers the N-glycan to a specific polypeptide acceptor site further described below and releases the heptasaccharide in its free form. Inactivation of the transferase leads to the N-glycan or N-glycan derivative being exclusively bound to the O-antigen acceptor Lipid A core in *E. coli* and leads to the exchange of GlcNAc for diN-acetylbacillosamine since the *E. coli* O-antigen ligase only recognizes GlcNAc-containing glycans at the attachment site (ie reducing end).

In a related embodiment the pgl derivative is one wherein one or more genes for di-N-acetylbacillosamine biosynthesis, pglD, E, F, and transfer are inactivated and the pglB gene is inactivated, too. This embodiment leads to the exchange of GlcNAc for di-N-acetylbacillosamine. The incorporation of such a pgl derivative in Salmonella resulted in increased cellular presentation and to the transfer of the modified heptasaccharide to Lipid A core instead of to polypeptide acceptors (see, U.S. Patent Application Publication No. 2012/0100177).

The at least one N-glycan of *C. jejuni*, or heptasaccharide derivative thereof, can be any N-glycan produced by any pgl operon of *Campylobacter*, or a functional derivative thereof, provided that the glycan is immunogenic, in that it elicits an immune response specific for a *Campylobacter* species.

In a specific embodiment, the glycan is the heptasaccharide of formula (I) as described above, i.e. GalNAc-α1,4-GalNAc-α1,4-[Glc-β-1,3]GalNAc-α1,4-GalNAc-α1,4-GalNAc-α1,3-diNAcBac, wherein diNAcBac (also termed di-N-acetylbacillosamine) is 2,4-diacetamido-2,4,6-trideoxy-D-glucopyranose.

The alternative embodiment, in which a pgl operon where the genes for di-N-acetylbacillosamine biosynthesis are inactivated, or mostly or completely deleted, leads to the synthesis of a derivative heptasaccharide of formula (II), being GalNAc-α1,4-GalNAc-α1,4-[Glc-β-1,3]GalNAc-α1,4-GalNAc-α1,4-GalNAc-α1,3-GlcNAc.

In a certain embodiment the N-glycan(s) or derivative(s) resulting from at least one pgl operon, or derivative thereof, can be linked to at least one homologous or heterologous *E. coli* polypeptide that will eventually be transferred to and presented on the cell surface. The polypeptide linked to the N-glycan (derivative) may be any type of polypeptide such as a pure polypeptide (only amino acids) or a post-translationally modified polypeptide, e.g. a lipid-linked polypeptide.

In another embodiment, the glycan(s) or derivative(s) thereof, are purified from the native host in their free oligosaccharide form and then chemically conjugated to a polypeptide or lipid carrier.

In a specific embodiment at least one glycan or derivative thereof resulting from the at least one pgl operon or derivative thereof is linked to the *E. coli* Lipid A core or a functionally equivalent derivative thereof. The Lipid A core of *E. coli* is an oligosaccharide structure consisting, but not limited to hexoses, heptoses and KDO (3-deoxy-D-mannooctulosonic acid) linked through two glucosamines to acyl chains anchoring the structure in the outer membrane of the bacterium. A functionally equivalent derivative of the Lipid A core is one capable of accepting one or more glycans or derivatives thereof and presenting them on the cell surface. It is noted that in this case the heptasaccharide or derivative thereof is not N-linked because the *E. coli* structure Lipid A core is not a polypeptide.

Optionally at least one heptasaccharide or derivative thereof takes the place of the O-antigen side chains in LPS (lipopolysaccharide). The inner and outer Lipid A core of *E. coli* remains unchanged while O-antigen biosynthesis is abolished through mutation of, for example, wzy and/or other mutations. In certain embodiments, at least one heptasaccharide, a derivative thereof, or a mixture of both, is expressed simultaneously with the O-antigen side chains in LPS resulting in heterogeneous LPS containing both the host O-antigen and the heptasaccharide.

It is preferred and for medical uses highly important that the *E. coli* strain of the invention does not elicit pathogenic effects when administered to an animal or human in live and/or inactivated form. The skilled person is aware of many ways of attenuating virulent *E. coli* species by mutation. For example, mutations that attenuate pathogenic *E. coli* (1) a CarAB mutant of the avian pathogenic *Escherichia coli* O2 is attenuated and effective as a live oral vaccine against colibacillosis in turkeys (Kwaga et al. *Infect Immun.* 62: 3766-3772, 1994); (2) mutation of the RNA chaperone Hfq significantly reduces pathogenicity of VTEC, EAEC, and UPEC in the nematode model (Bojer et al. *Microbes Infect* 14:1034-1039, 2012); (3) mutations of genes within the phosphate-specific transport system (Pst) attenuate *E. coli* strains (Buckles et al. *Microbiology* 152: 153-160, 2006; Daigle et al. *Infect and Immun.* 63: 4924-4927, 1995).

In a particular embodiment the *E. coli* strain employed in the vaccine composition is attenuated by partial or full inactivation of the expression of the O-antigen, for example, by mutation in the wzy gene (resulting in an O-antigen polymerase mutant) (Baba et al. *Mol. Syst. Biol.* 2: 2006).

The above-described *E. coli* strains are highly immunogenic and produce immune responses against *Campylobacter*, such as *C. jejuni*, infections. Furthermore, once prepared they can be easily propagated and mass-produced. They can be administered as dead or live vaccines, live vaccines allowing for prolonged propagation and sustained immune stimulus in the host as well as full immune responses with or without adjuvants.

Therefore, the present application also relates to the medical use of live or dead *E. coli* strains engineered to present one or more *Camplyobacter* N-glycans, or derivatives thereof, on its surface, in particular for preparing a medicament, preferably a vaccine.

Preferably, the medicament is useful for the prevention and/or treatment of *C. jejuni* infection and/or colonization, preferably in livestock, more preferably in cattle and poultry, most preferably in poultry such as chicken, turkey, goose and ducks.

In accordance with one aspect, the present application provides a vaccine composition that is a pharmaceutical composition, food or feed (additive) comprising dead or live *E. coli* engineered to present one or more *Campylobacter* N-glycans, or derivatives thereof, on its surface, and a physiologically acceptable excipient, diluent or carrier. Optionally, the vaccine composition includes, or is administered with additional components, such as, for example, an adjuvant. In another alternative, the vaccine composition described herein is formulated for administration with another vaccine composition.

Adjuvants in general comprise substances that boost the immune response of the host in a non-specific manner. A number of different adjuvants are known in the art. Examples of adjuvants are Freunds Complete and Incomplete adjuvant, vitamin E, non-ionic block polymers and polyamines such as dextransulphate, carbopol and pyran. Also suitable are surface active substances such as Span, Tween, hexadecylamine, lysolecitin, methoxyhexadecylglycerol and saponins (e.g., Quil A®). Furthermore, peptides such as muramyldipeptides, dimethylglycine, and tuftsin, are often used. Next to these adjuvants, Immune-stimulating Complexes (ISCOMS), mineral oil e.g. Bayol® or Markol®, vegetable oils or emulsions thereof and Diluvac® Forte can advantageously be used.

Optionally, the vaccine is mixed with one or more stabilisers, e.g., to protect degradation-prone components from being degraded, to enhance the shelf-life of the vaccine, or to improve freeze drying efficiency. Useful stabilisers are, for example, SPGA (Bovarnik et al. *J. Bacteriology* 59: 509, 1950), skimmed milk, gelatin, bovine serum albumin, carbohydrates e.g. sorbitol mannitol, trehalose, starch, sucrose, dextran or glucose, proteins such as albumin or casein or degradation products thereof, and buffers, such as alkali metal phosphates.

The vaccine composition can be in the form of, for example, a solution, suspension, or a freeze-dried composition suitable for reconstitution prior to administration.

Freeze-drying is an efficient method for preservation of the vaccine composition. Freeze-dried material can be stored stable for many years. Storage temperatures for freeze-dried material may well be above zero degrees, without being detrimental to the material. Freeze-drying can be done according to all well-known standard freeze-drying procedures.

Method of immunization

The present application provides a method of immunizing an animal against *Campylobacter* infection. The method comprises the step of administering to the animal a vaccine composition comprising recombinant *E. coli* that has been engineered to present at least one *Campylobacter* N-glycan, or heptasaccharide derivative thereof, on its surface, as described above.

Campylobacteriosis is the disease caused by infection with *Campylobacter*. The most common symptoms are diarrhea, abdominal pain, fever, headache, nausea, and/or vomiting. Typically these symptoms only last for about three to six days. However, rarely, *Campylobacter* infection can cause lasting complications such as, for example, Guillain-Barré Syndrome (GBS), arthritis and bacteremia. Accordingly, the vaccines described herein are useful in immunizing animals, including humans and livestock, such as chicken which is a leading cause of human foodborne illness. Accordingly, the present application further provides a method for preventing or minimizing the effect of a disease or disorder caused by *Campylobacter* infection. In specific embodiments, the disease or disorder caused by *Campylobacter* infection is campylobacteriosis, Guillain-Barré Syndrome (GBS) and/or arthritis and/or bacteremia, although other *Campylobacter* species have been linked with other illnesses such as periodontitis and abortions.

In the embodiment in which the vaccine composition is used to vaccinate livestock, there are various routes for administration of the composition that can be convenient for mass vaccination. Administration can be performed via drinking water, food or feed, spray/nebulisation (e.g., to day old chickens in delivery boxes, or to animals in a housed environment, such as a poultry house), eye drop, transfixion and scarification (cutaneous route in the wing web or foot), injection (e.g., intramuscular or subcutaneous), or in-ovo administration.

Optionally, animals are treated with an initial dose of vaccine composition followed by one or more booster doses at appropriate time intervals. A worker skilled in the art would readily identify the dose amount and dosing scheduling appropriate for a particular application. In the current example, we do an initial vaccination in 1 week old birds with $1 \times 10^8$ live or formalin fixed *E. coli* cells (or with any other glycoconjugated vaccine i.e. the *C. jejuni* N-glycan linked to ToxC). We perform one boost with the same amount of bacterial cells (or protein) two weeks later. Challenge with campylobacter is usually done after another week and the birds are euthanized 1 week after the challenge (as described below).

To gain a better understanding of the invention described herein, the following example is set forth. It should be understood that these examples are for illustrative purposes only. Therefore, they should not limit the scope of this invention in any way.

EXAMPLES

Example 1

Preparation of Vaccine

*Campylobacter jejuni* N-glycan Fused to a Protein

Expression and purification of the ToxC-GT protein glycosylated with the *C. jejuni* N-glycan: The ToxC-GT protein glycosylated with the *C. jejuni* N-glycan was expressed in *E. coli* BL21 expressing the *C. jejuni* pgl operon and purified by Ni-NTA chromatography as described in international published PCT Application No WO 2012/027850. The protein was further purified by ion exchange chromatography using an AEKTA FPLC system equipped with a 2.5 ml MonoQ anion exchange column. The mobile phase was 50 mM Tris-HCl buffer, pH 8.0 with a NaCl gradient set to 0-500 mM NaCl over 30 column volumes. Fractions containing the glycoconjugate were analysed by 12.5% SDS PAGE, passed twice through 1 g of lipid removal absorbent (LRA, Supelco), dialyzed against sterile PBS and set to a concentration of 0.5 mg/ml protein prior to use. The protein concentration was determined using standard methodologies (Bradford test) using increasing concentrations of BSA in PBS to create a standard curve.

*Campylobacter jejuni* N-glycan fused to the Lipid A core structure of *E. coli*: Preparation of the *E. coli* Vaccine

*E. coli* cells expressing the *C. jejuni* heptasaccharide were described previously (Nothaft et al. Molecular and Cellular Proteomics 11: 1203-1219). Cells were grown in liquid broth (2×YT Broth (Yeast extract and tryptone broth)) at 37° C. under vigorous shaking (220 rpm) until stationary phase was reached. Cells were harvested by centrifugation and washed twice with sterile PBS. The amount of cells was determined by plating serial dilutions of a cell suspension set to an $OD_{600}$ of 2.0 and used either directly or formalin-fixed.

Cells of an *E. coli* overnight culture expressing the *C. jejuni* pgl locus were harvested by centrifugation and washed twice with sterile PBS buffer as described in Nothaft et al. *Mol. Cell. Proteomics* 11: 1203-1219, 2012. Then, 1 ml of cells, adjusted to an $OD_{600}$ with sterile PBS to 1.0 were centrifuged and re-suspended in 100 μl of 1-fold Laemmli sample buffer and heated for 10 min at 95° C. Proteinase K was added to a final concentration of 200 μg/ml and the sample was incubated at 60° C. for 1 h followed by 5 min incubation on ice and centrifugation for 15 min. Aliquots of the supernatant were separated by standard 12 0.5% SDS-PAGE. The heptasaccharide fused to the Lipid A core was visualized by Western Blotting as described (Nothaft et al. Molecular and Cellular Proteomics 11: 1203-1219) using the *Campylobacter jejuni* N-glycan specific antiserum hR6 as primary and anti-rabbit conjugated with alkaline phosphatase as a secondary antibody (FIG. 1). Lane 1 shows proteinase K treated cell lysates from the *E. coli* O-antigen polymerase mutant expressing the protein glycosylation operon of *C. jejuni* with an inactive pglB gene (pACYC184pglB$_{mut}$). Formation of the Lipid A-N-glycan fusion is marked by an arrow. Lane 2 shows proteinase K treated cell lysates from the *E. coli* O-antigen polymerase mutant empty vector control (pACYC184). Molecular weight markers (MW in kilodaltons, kDA) are indicated on the left. The higher molecular weight bands are components of *E. coli* that are cross-reactive in both preparations.

Figure 2:
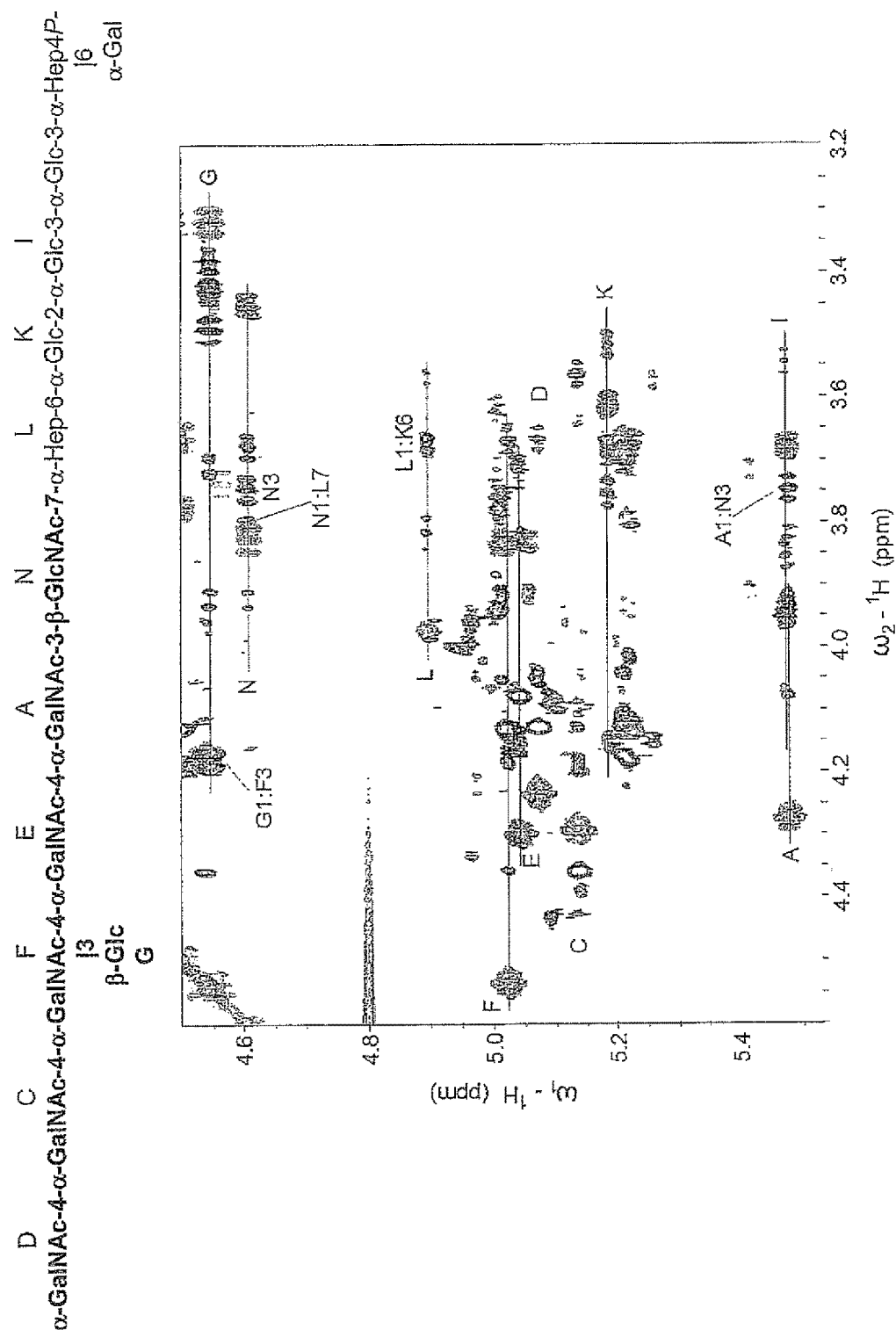
FIG. 2 shows the structure of the Lipid A-N-glycan and an NMR experiment of purified Lipid A-*Campylobacter jejuni* N-glycan component

Nuclear magnetic resonance spectroscopy (NMR) of the purified Lipid A-N-glycan component. Glycolipids were prepared from eight liters of an $OD_{600}=1.0$ *E. coli* O-antigen polymerase mutant culture expressing the protein glycosylation operon of *C. jejuni* with an inactive pglB gene (pACYC184pglB$_{mut}$). LPS was extracted by phenol-water, dialyzed, treated with AcOH to precipitate nucleic acids, dialyzed, dried, hydrolyzed with 2% AcOH, and separated on a Biogel P6. Fractions were analyzed by NMR. Fractions that contained *C. jejuni* N-glycan signals were combined and separated on an anion-exchange Hitrap column using a NaCl gradient. Fractions were analyzed by NMR. Fractions containing *C. jejuni* N-glycan signals were desalted by Sephadex G-15 chromatography. Connections were confirmed by Nuclear Overhauser effect spectroscopy (NOESY) and Heteronuclear multiple-bond correlation spectroscopy (HMBC). Specific *C. jejuni* N-glycan chemical shifts could be observed, all 1-4-linkages of the *C. jejuni* N-glycan components gave transglycosidic NOE 1:4 and 1:6 and assignments were in good agreement with previously published data (FIG. 2 and Table 1, and Nothaft et al. Molecular and Cellular Proteomics 11: 1203-1219, 2012). The derivative of the *C. jejuni* N-glycan with a GlcNAc instead of diNAcBac as reducing end sugar (FIG. 2) was attached via O-7 of the L-glycero-D-manno-heptose of the Lipid A core. All signals of Hep (L) were found by the analysis of main heap of correlations and assignments for the *E. coli* Lipid A core part were in agreement with published data (Muller-Loennies et al. Journal of Biological Chemistry 278:,34090-34101, 2003, and Table 1).

TABLE 1

| | | Chemical shifts | | | | | | |
|---|---|---|---|---|---|---|---|---|
| | | 1 | 2 | 3 | 4 | 5 | 6 | 7 |
| α-GalNAc A | $\delta_H$ | 5.47 | 4.27 | 3.23 | 4.07 | 3.92 | 3.70; 3.75 | |
| | $\delta_C$ | 98.2 | 51.0 | 68.0 | 77.6 | 72.7 | 60.8 | |
| α-GalNAc C | $\delta_H$ | 5.13 | 4.29 | 4.19 | 4.13 | 4.49 | 3.66; 3.78 | |
| | $\delta_C$ | 98.2 | 51.5 | 67.8 | 77.4 | 71.6 | 59.9 | |
| α-GalNAc D | $\delta_H$ | 5.07 | 4.23 | 4.04 | 4.06 | 4.39 | 3.70; 3.73 | |
| | $\delta_C$ | 99.3 | 51.4 | 68.4 | 69.6 | 71.9 | 61.8 | |
| α-GalNAc E | $\delta_H$ | 5.04 | 4.30 | 4.15 | 4.13 | 4.43 | 3.65; 3.68 | |
| | $\delta_C$ | 99.3 | 51.5 | 67.8 | 77.4 | 72.3 | 60.5 | |
| α-GalNAc F | $\delta_H$ | 5.02 | 4.53 | 4.17 | 4.36 | 4.45 | 3.56; 3.64 | |
| | $\delta_C$ | 99.5 | 50.5 | 67.8 | 75.6 | 72.3 | 60.3 | |
| β-Glc G | $\delta_H$ | 4.60 | 3.32 | 3.48 | 3.38 | 3.43 | 3.71; 3.92 | |
| | $\delta_c$ | | 74.1 | 76.8 | 70.9 | 76.9 | 61.8 | |
| α-GlcNAc N | $\delta_H$ | 4.54 | 3.82 | 3.74 | 3.68 | 3.45 | 3.75; 3.92 | |
| | $\delta_c$ | | 55.3 | 79.6 | 72.3 | 76.9 | 61.9 | |
| α-Hep L | $\delta_H$ | 4.89 | 3.97 | 3.80 | 3.86 | 3.57 | 4.16 | 3.80; 4.01 |
| | $\delta_C$ | 100.4 | 71.1 | 72.0 | 67.3 | 72.8 | 68.4 | 73.2 |
| α-Glc K | $\delta_H$ | 5.18 | 3.61 | 3.75 | 3.51 | 4.15 | 3.67; 3.92 | |
| | $\delta_C$ | 97.1 | 72.4 | 74.6 | 70.4 | 71.2 | 65.9 | |
| α-Glc I | $\delta_H$ | 5.47 | 3.68 | 3.85 | 3.54 | 4.08 | 3.82; 3.90 | |
| | $\delta_C$ | 98.2 | 76.8 | 72.1 | 70.3 | 72.6 | 61.2 | |

Figure 3:
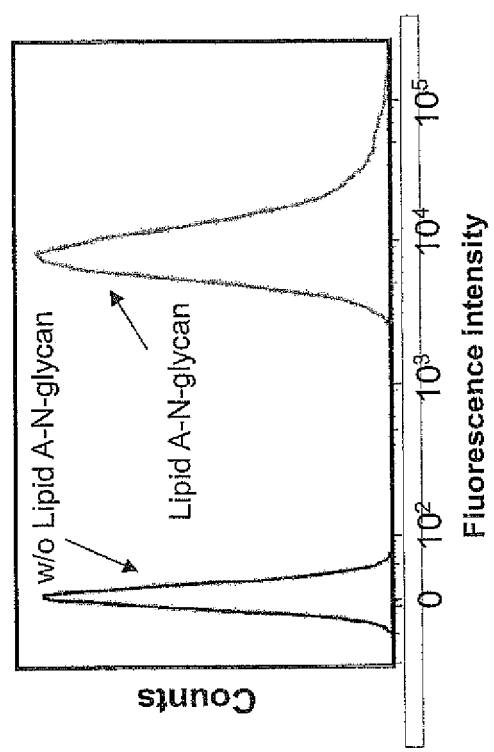
FIG. 3 shows a FACS experiment with the *E. coli* polymerase mutant.

Fluorescence Activated Cell Sorting (FACS) analysis. First, 1 ml of $OD_{600}$=1.0 *E. coli* cells were pelleted by centrifugation and resuspended in 1 ml blocking solution (PBS, 5% skim milk). Cells were probed with *C. jejuni* N-glycan-specific antiserum hR6 and Alexa Flour-546 conjugated anti-Rabbit antiserum and analyzed by FACS. FACS data were processed with the FACS Diva software. DAPI counter-staining was used to identify and gate for intact cells. Analysis of a population of $2 \times 10^4$ cells showed a significant increase in fluorescence for *E. coli* cells expressing the *C. jejuni* N-glycan compared to *E. coli* empty vector control (pACYC184) cells confirming that the *C. jejuni* N-glycan is presented on the cell surface (FIG. 3). The peak appearance and peak geometry shows that each *E. coli* cell presented a comparable amount of the *C. jejuni* N-glycan on its surface.

Example 2

Vaccination and Challenge

Figure 4B:
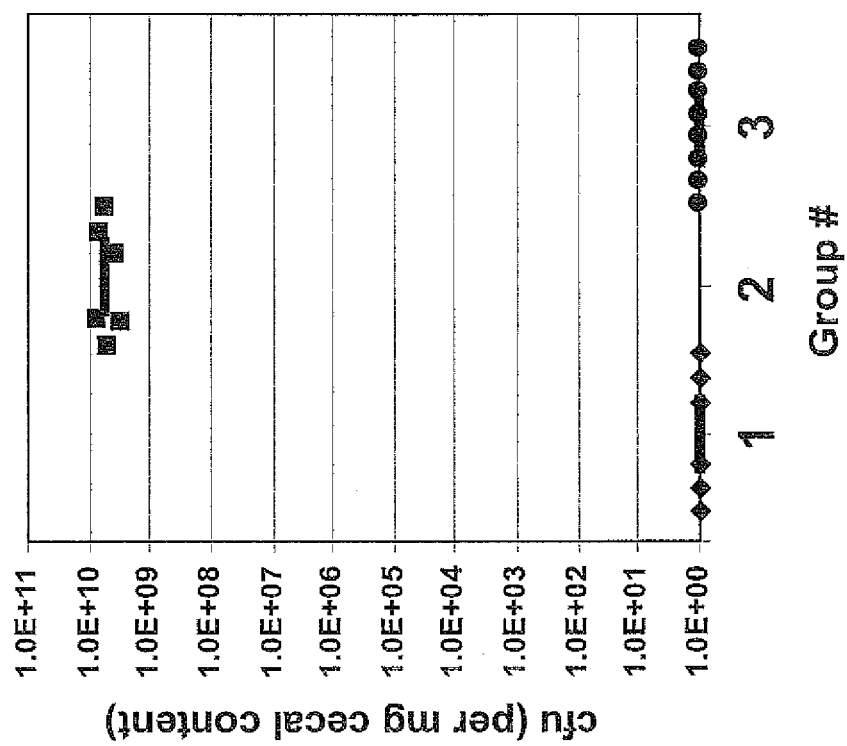
FIGS. 4 A, B, C and D depict vaccination and challenge experiments as described in Example 2 and FIG. 5 A and B depict chicken IgY (IgG) N-glycan specific antibody responses (ELISA).

Exposure of chickens to injections of the ToxC-GT glycoconjugate (FIG. 4D) or oral doses of dead (FIG. 4A) as well as live (FIG. 4B and C) strains of the modified *E. coli* described in Example 1, resulted in significant decreases in the cecal content of *Campylobacter* in challenged chickens. Three chicken vaccination experiments were carried out using *E. coli* expressing the *C. jejuni* heptasaccharide to demonstrate increased immunity of chicks to Campylobacter. The results of these experiments are shown in FIGS. 4A, B and C.

In the first chicken vaccination experiment, a challenge was carried out with three groups of chicks. The control PBS group contained four chickens while groups 2 and 3 each contained eight chickens. The conditions for groups 1 and 2 are shown in Table 2. Group 3 was orally gavaged with dead *E. coli* cells surface expressing *C. jejuni* N-glycan heptasaccharide on days 7 and 21. Birds were subsequently challenged as follows: Group 1 (negative control) was orally gavaged with 300 µl PBS; groups 2 and 3 were orally gavaged with 300 µl PBS containing $10^2$ *C. jejuni* 81-176 cells. On day 35, chickens were euthanized and colonization levels were determined by plating serial dilutions of the cecal contents of each bird on selective Karmali agar. Colony forming units (cfu) were determined after incubation of the plates for 48 hrs under microaerobic conditions. The results are graphically shown in FIG. 4A, with colonization levels shown as cfu per gram cecal content. The horizontal bars represent the median for each group. Specifically, the results show that the N-glycan-based vaccine reduces *Campylobacter* colonization in chickens. No colony forming units were detected on plates of group 1 (PBS control) whereas group 2 birds were colonized with an average of approximately $10^{10}$ campylobacter cells per gram cecal content. Colonization was reduced in group 3 by approximately 4 logs.

In the second chicken vaccination experiment a challenge was carried out with three groups of chicks. Groups 1 and 2 contained 6 chickens, group 3 contained 8 chickens. The conditions for groups 1 and 2 are shown in Table 2. Group 3 was orally gavaged with live *E. coli* cells expressing the *C. jejuni* N-glycan heptasaccharide on days 7 and 21. Challenge concentrations and colonization levels were determined as described in the first experiment. The results are graphically shown in FIG. 4B, with colonization levels shown as cfu per gram cecal content. The horizontal bars represent the median for each group. The results show that the N-glycan-based vaccine reduces *Campylobacter* colonization in chickens. No colony forming units were detected on plates of group 1 (PBS control) whereas group 2 birds were colonized with an average of approximately $10^{10}$ campylobacter cells per gram cecal content. Colonization was not detectable in any of the birds in group 3.

In the third experiment shown in FIG. 4C, a challenge was carried out with 4 groups of chicks. Groups 1 contained 6 chickens, groups 2, 3 and 4 contained 8 chickens. The conditions for groups 1 and 2 are shown in Table 2. Groups 3 and 4 were orally gavaged on day 7 and day 21. Group 3 birds received live *E. coli* not expressing the N-glycan on the surface while group 4 birds received live *E. coli* cells expressing the *C. jejuni* N-glycan heptasaccharide on their surfaces. The results are graphically shown in FIG. 4C, with colonization levels shown as cfu per gram cecal content. The horizontal bars represent the median for each group. The results show that the N-glycan-based vaccine repeatably reduces *Campylobacter* colonization in chickens and that *E. coli* cells not expressing the N-glycan do not have a probiotic effect since the *Campylobacter* colonization levels after challenge were similar to the group 2 birds.

In the fourth experiment shown in FIG. 4D, a challenge was carried out with six groups of chicks, each group containing eight chickens. The conditions of each group are shown in Table 2.

TABLE 2

Challenge groups

| Group | Condition |
|---|---|
| 1 | Negative control: no exposure to antigen and no challenge |
| 2 | Positive control: no exposure to antigen |
| 3 | Single IM dose glycoprotein antigen on day 21 |
| 4 | Single IM dose glycoprotein antigen on day 7 |
| 5 | Doses of glycoprotein antigen IM on days 7 and 21 |
| 6 | Oral gavage of live *E. coli* cells surface expressing *C. jejuni* N-glycan heptasaccharide on days 7 and 21 |

Similar to the previous experiments, on day 1, cloacal swabs were performed on 10% of birds (5 randomly selected) and plated onto selective Karmali agar to confirm the birds were not colonized with *C. jejuni*. No *Campylobacter* colonies were observed after 48 hrs of incubation under microaerobic conditions at 37° C.

Similar to the previous experiments, on day 7, up to 50 µl of blood (pre-bleed) was collected from each bird. Sera were prepared as follows: After keeping the blood samples at 37° C. for 1 hr followed by centrifugation (5 min, 18.000×g, 4° C.) the supernatants (sera) were transferred to a fresh tube and glycerol was added to a final concentration of 10%. Sera were stored at −20° C. until further use. Subsequent antimicrobial treatment was performed as follows: Group 1 (PBS control) and 2 (colonization control) received 300 µl of PBS with Freunds complete on day 7 and the same amount but with Freunds incomplete adjuvant on day 21 (150 µl PBS+150 µl adjuvant) injected at two sites in the chest with 150 µl of vaccine formulation (without the glycoconjugate) per site. Group 3 received no antigen on day 7 but received one dose of ToxC-GT glycosylated with the *C. jejuni* N-glycan (100 µg protein in 150 µl PBS+150 µl of Freunds complete adjuvant) on day 21; Group 4 received one dose of ToxC-GT glycosylated with the *C. jejuni* N-glycan in Freunds complete adjuvant on day 7 and no antigen on day 21. Group 5 received 2 doses (on day 7 with Freunds complete and on day 21 with Freunds incomplete as adjuvant) of 100 µg ToxC-GT with the *C. jejuni* N-glycan injected in the leg (150 µl of vaccine formulation in each leg) and group 6 was orally gavaged with 2 doses (on day 7 and day 21) with 300 µl PBS containing $10^8$ live *E. coli* cells expressing the *C. jejuni* N-glycan on their surface.

Similar to the previous experiments, on day 28, 100 µl of blood was drawn from each bird (test bleed) of groups 1-6 and sera were prepared and stored as described above. Birds were subsequently challenged as follows: Group 1 (negative control) was orally gavaged with 300 µl PBS; groups 2-6 were orally gavaged with 300 µl PBS containing $10^2$ *C. jejuni* 81-176 cells. On day 34, chickens were euthanized, blood (final bleed) was taken via heart puncture and sera were prepared and stored as described above. Colonization levels were determined by plating serial dilutions of the cecal content of each bird on selective Karmali agar. Colony forming units (cfu) were determined after incubation of the plates for 48 hrs under microaerobic conditions.

The results are graphically shown in FIG. 4D, with colonization levels shown as cfu per gram cecal content. The horizontal bars represent the median for each group. Specifically, the results again show that N-glycan-based vaccines reduce *Campylobacter* colonization in chicken and that vaccines comprised of live *E. coli* cells expressing the *C. jejuni* N-glycan on their surface perform better than glycoprotein vaccines in chickens (see below).

No colony forming units were detected on plates of group 1 (PBS control) whereas group 2 birds were colonized with an average of approximately $10^{10}$ campylobacter cells per gram cecal content. Colonization was reduced in group 3, group 4 and group 5 with an average cfu of $2.2×10^4$, $6.8×10^5$ and $5.5×10^4$ per gram cecal content, respectively.

Colonization in group 6 was almost abolished with an average of 100 cfu per gram cecal content. In addition, 5 out of 8 birds showed no signs of *C. jejuni* colonization at all. This clearly indicated that treatment with the protein based *C. jejuni*-N-glycan vaccine resulted in reduced colonization after challenge with *Campylobacter* independent on the time point of injection and the application site of the vaccine and that oral vaccination with live *E. coli* cells that expressed the heptasaccharide on their surface almost completely abolished *Campylobacter* colonization. Moreover, the self limitation of the *E. coli* vaccine strain was demonstrated since no *E. coli* was observed in cecal contents of this group when plated on selective LB Kan-Cm. The elimination of the live *E. coli* vaccine strain from chickens was observed in all experiments.

ELISA tests were performed to analyze the N-glycan-specific immune response, specifically the chicken IgY (IgG) N-glycan specific antibody response. Free oligosaccharide (fOS) from *C. jejuni* was prepared as described (Dwivedi et al. *Biopolymers*, 99: 772-7830, 2013) and coupled to BSA by reductive amination as described (Nothaft et al. *Mol. Cell. Proteomics* 11: 1203-1219, 2012). Formation of the BSA-Cj-N-glycan conjugate was confirmed by Western Blotting using the R1-4 antiserum. After adjusting the concentration to 1 mg/ml with PBS, the glycoconjugate was stored at 4° C. until further use. Then 96-well Maxisorb plates were coated with 500 ng of BSA-Cj-N-glycan conjugate overnight (18 hrs) at 4° C. After removal of unbound antigen, the plate was blocked for 1 hr at RT with 100 µl PBS-T, 5% skim milk with shaking. After discarding the blocking solution, 100 µl of the antibody solutions were added and incubated for 1 hr as described above. Antibody solutions were comprised of N-glycan-specific antiserum diluted 1:3000 in PBS-T, 1% skim milk or chicken serum (prepared from the $2^{nd}$ bleed (ie day 28) of the vaccination experiments) and diluted 1:50 in PBS-T, 1% skim milk. Plates were incubated for 1 hr at RT as described and each well was washed 3 times for 5 min with 100 µl of PBS-T. After addition of 100 µl of the secondary antibody solution (either anti-rabbit-AP (1:500) for the R1-4 control, or anti chicken IgY (1:500) for the experimental samples and incubated for 1 hr at RT, the secondary antibody solutions were discarded and the wells were washed 4-times 5 min with 100 µl of PBS-T. After the last washing step, the remaining washing solution was completely removed from each well and the plate was developed using PNPP as a substrate. Immunoreactivity in each serum was determined after scanning the plate at $OD_{405}$ in a plate reader.

Figure 5A:
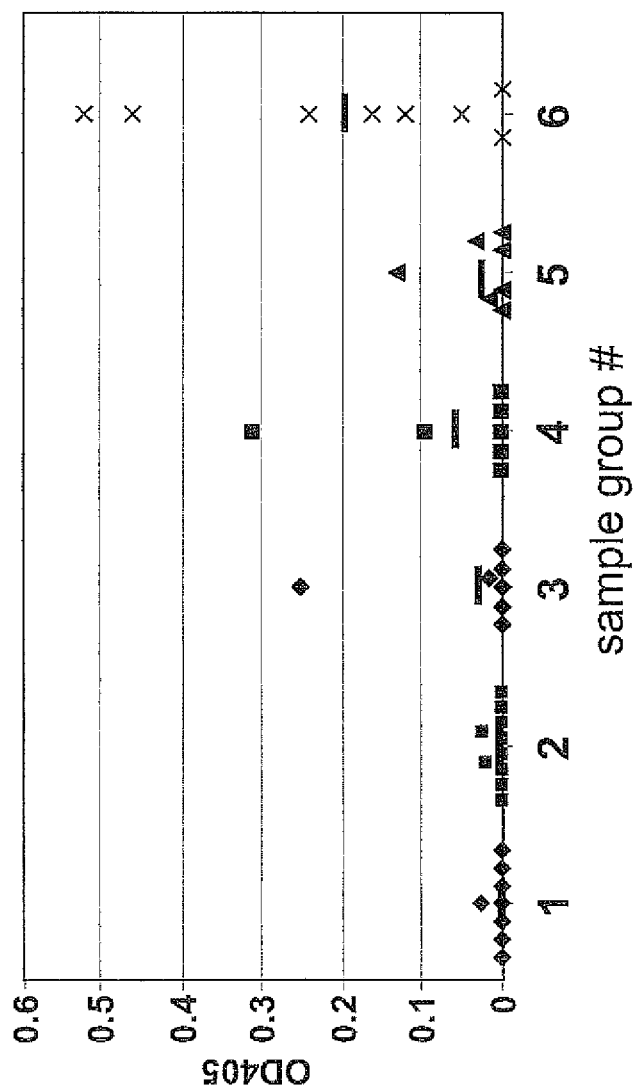

*C. jejuni* N-glycan-specific antibodies were present (FIG. 5A) in sera prepared from blood drawn on day 28 prior to the challenge with *Campylobacter* from birds vaccinated with 1 dose of ToxC-GT with glycan on day 21 (chest, IM)(sample group 3), 2 doses ToxC-GT with glycan on day 7 & 21 (chest, IM) (sample group 4), 2 doses ToxC-GT with glycan on day 7 & 21 (leg) (sample group 5), and 2 doses dead *E. coli* (sample group 6). The antibody response (expressed as $OD_{405}$) was highest in sample group 6 and the majority of chickens in this sample group showed no colonization. The antibody response in the positive and negative colonization control groups (sample groups 1 and 2) was below the limit of detection. The horizontal bars represent the median for each group.

Figure 5B:
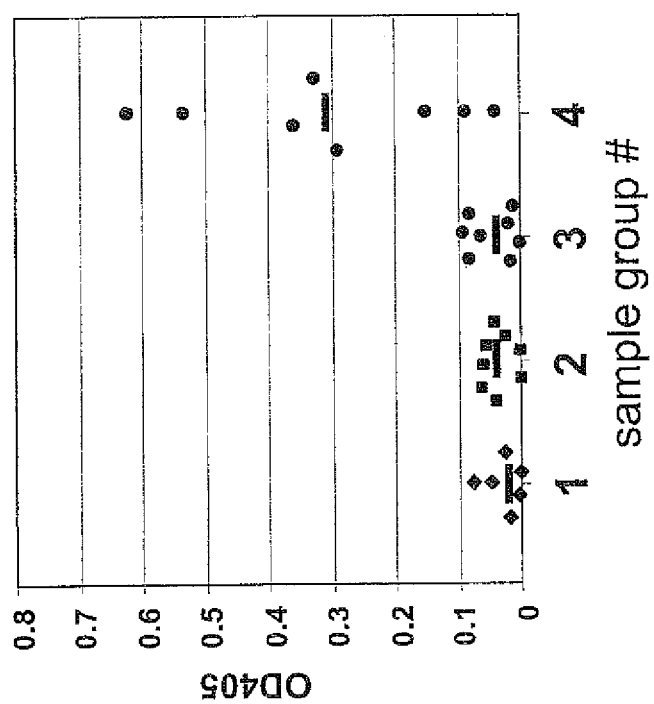

*C. jejuni* N-glycan-specific antibodies were present (FIG. 5B) in sera prepared from blood drawn on day 28 prior to the challenge with *Campylobacter* from birds vaccinated with live *E. coli* presenting the N-glycan on the surface (sample group 4). This corresponds to vaccine experiment #3 shown in FIG. 4C. The antibody responses (expressed as $OD_{405}$) in birds vaccinated with live *E. coli* no glycan (sample group 3) and the positive and negative colonization control groups (sample groups 1 and 2) were below the limit of detection. The horizontal bars represent the median for each group.

The following was observed:
1) feeding chicks the dead *E. coli* cells expressing the *C. jejuni* heptasaccharide followed by challenge with *C. jejuni* caused a reduction of approximately 4 logs in *C. jejuni* colonization of the chicken gut (FIG. 4A); and
2) feeding chicks the live *E. coli* cells expressing the *C. jejuni* heptasaccharide followed by challenge with *C. jejuni* consistently caused a reduction greater than 7 logs in *C. jejuni* colonization of the chicken gut (FIGS. 4B, C and D).

It is evident that vaccines comprising either dead or live *E. coli* cells expressing the *C. jejuni* heptasaccharide are capable of significantly increasing immunity of chicks to later challenge by *C. jejuni*.

Control Experiment

In order to demonstrate that the drop in *C. jejuni* colonization is a result of vaccination with live *E. coli* expressing the *C. jejuni* heptasaccharide and not to a probiotic effect due to exposure to live *E. coli* cells, the cecal contents from birds that were vaccinated with the live *E. coli* strains were also plated onto *E. coli* selective media as mentioned above. No *E. coli* colonies were detected in the chickens vaccinated with live *E. coli* indicating that the *E. coli* was cleared prior to termination of the experiment.

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A method of vaccinating an animal against *Campylobacter*, the method comprising:
   administering to an animal a vaccine composition comprising:
   *E. coli* engineered with a *Campylobacter* pgl operon lacking a functional *pglB* gene to express at least one N-glycan of *Campylobacter* or an N-glycan derivative thereof on its cell surface; and one or more of a physiologically acceptable diluent, excipient, adjuvant or carrier, wherein the *E. coli* is engineered to be partially or fully deficient in the expression of O-antigen, and wherein the N-glycan is expressed on the surface of *E. coli* as a Lipid A core fusion.

2. The method of claim 1, wherein the *Campylobacter* is *C. jejuni*.

3. The method of claim 1, wherein the animal is avian.

4. The method of claim 3, wherein the avian is a chicken.

5. The method of claim 1, wherein the animal is a mammal.

6. The method of claim 5, wherein the mammal is a human.

7. The method according to claim 1, wherein the vaccine composition is administered by spraying or in a pharmaceutical composition, food, a feed additive, or drinking water.

8. The method according to claim 7, wherein the pharmaceutical composition is formulated for administration by oral administration, in ovo administration, injection or infusion.

9. The method according to claim 1, comprising a second step of administering the vaccine composition.

10. The method of claim 1 wherein the N-glycan comprises a single heptasaccharide N-glycan.

11. The method of claim 10 wherein the single full length N-glycan is attached via O-7 of L-glycero-D-manno-heptose of the Lipid A core.

12. The method of claim 1 wherein the *E. coli* is attenuated by mutation in a wzy gene.

* * * * *